United States Patent [19]
Barker et al.

[11] Patent Number: 5,261,548
[45] Date of Patent: * Nov. 16, 1993

[54] INDICATOR CAP FOR USE WITH THREADED OR BAYONET LUG CONTAINER

[75] Inventors: Allan Barker; Gage Garby, both of Boulder, Colo.

[73] Assignee: Senetics, Inc., Boulder, Colo.

[*] Notice: The portion of the term of this patent subsequent to Apr. 23, 2008 has been disclaimed.

[21] Appl. No.: 21,735

[22] Filed: Feb. 23, 1993

Related U.S. Application Data

[63] Continuation of Ser. No. 718,354, Jun. 21, 1991, abandoned, which is a continuation-in-part of Ser. No. 641,759, Jan. 17, 1991, which is a continuation-in-part of Ser. No. 306,485, Feb. 3, 1989, Pat. No. 5,009,338.

[51] Int. Cl.$^5$ .................... B65D 55/02; B65D 51/18
[52] U.S. Cl. .................... 215/230; 215/203; 215/216; 215/218; 215/220; 215/301; 206/534
[58] Field of Search ............... 215/203, 204, 216, 218, 215/219, 230, 250, 301, 334; 206/459.1, 534

[56] References Cited

U.S. PATENT DOCUMENTS

| | | |
|---|---|---|
| 498,851 | 3/1893 | Adsit . |
| 2,587,147 | 2/1952 | Guion . |
| 2,644,452 | 7/1953 | Brown . |
| 2,767,680 | 10/1956 | Lerner . |
| 2,939,597 | 7/1960 | Greene . |
| 2,943,730 | 7/1960 | Tregilgas . |
| 3,073,468 | 1/1963 | Arneson ................ 215/230 |
| 3,120,318 | 2/1964 | Rigor ................ 215/218 X |
| 3,151,599 | 10/1964 | Livingston . |
| 3,334,731 | 8/1967 | Dale . |
| 3,446,179 | 5/1969 | Bender . |
| 3,753,417 | 8/1973 | Garby . |
| 3,766,882 | 10/1973 | Babbitt . |
| 3,887,099 | 6/1975 | Gillman . |
| 3,921,568 | 11/1975 | Fish . |
| 3,926,326 | 12/1975 | Grau . |
| 3,960,713 | 6/1976 | Carey . |
| 3,977,554 | 8/1976 | Costa . |
| 3,996,879 | 12/1976 | Walton ................ 206/534 X |
| 4,011,829 | 3/1977 | Wachsmann et al. .......... 215/216 X |
| 4,029,033 | 6/1977 | Kerwin et al. ................ 220/359 |
| 4,069,935 | 1/1978 | Hampel ................ 215/203 |
| 4,069,942 | 1/1978 | Marshall et al. ................ 206/534 X |
| 4,078,661 | 3/1978 | Thomas ................ 206/534 X |
| 4,094,408 | 6/1978 | Ford . |
| 4,164,301 | 8/1979 | Thayer ................ 220/253 |

(List continued on next page.)

FOREIGN PATENT DOCUMENTS 0230323 1/1987 European Pat. Off. .

Primary Examiner—Allan N. Shoap
Assistant Examiner—Vanessa Caretto
Attorney, Agent, or Firm—Beaton & Swanson

[57] ABSTRACT

A closure for a container, including means for counting and indicating the number of times the closure has undergone a cycle of closing and opening the container, and further including means for incorporating the closure into means for resisting the opening of the container by a child. In a preferred embodiment, the closure includes an outer cover having an indicator symbol window an indicator symbol carrier rotatably mounted in the outer cover with indicator symbols visible through the indicator window, tooth and pawl means for allowing one-way rotation of the outer cover relative to the indicator symbol carrier to allow the advancement of the window and an audible click as the pawl passes over a tooth to confirm proper advancement, lost motion means for positively assuring the advancement of the window by one and only one indicator symbol upon each cycle, and a closure mechanism requiring the application of an axial force urging the closure toward the container while applying a rotational force to disengage the closure from the container.

7 Claims, 1 Drawing Sheet

U.S. PATENT DOCUMENTS

| | | |
|---|---|---|
| 4,345,541 | 8/1982 | Villa-Real . |
| 4,347,804 | 9/1982 | Villa-Real . |
| 4,357,192 | 11/1982 | Moser . |
| 4,405,045 | 9/1983 | Villa-Real . |
| 4,419,016 | 12/1983 | Zoltan . |
| 4,432,300 | 2/1984 | Lyss . |
| 4,440,306 | 4/1984 | Van Buskirk . |
| 4,489,834 | 12/1984 | Thackrey . |
| 4,500,005 | 2/1985 | Forrester . |
| 4,501,370 | 2/1985 | Kelley . |
| 4,511,050 | 4/1985 | Nicol . |
| 4,523,933 | 7/1985 | Allen . |
| 4,548,157 | 10/1985 | Hevoyan . |
| 4,562,933 | 1/1987 | Dennis . |
| 4,634,012 | 1/1987 | Kelley . |
| 4,641,759 | 2/1987 | Kelley . |
| 4,646,936 | 3/1987 | Frazier . |
| 4,662,520 | 5/1987 | Griffin . |
| 4,666,051 | 5/1987 | Trick . |
| 4,693,399 | 9/1987 | Hickman et al. ............... 220/339 X |
| 4,705,182 | 11/1987 | Newel-Lewis . |
| 4,723,673 | 2/1988 | Tartaglia . |
| 4,749,093 | 6/1988 | Trick . |
| 4,753,189 | 6/1988 | Mastman . |
| 4,782,966 | 11/1988 | Thackrey ............................ 215/230 |
| 4,920,912 | 5/1990 | Kirkling ........................ 206/534 X |
| 5,009,338 | 4/1991 | Barker ................................ 215/230 |
| 5,011,032 | 4/1991 | Rollman . |
| 5,082,129 | 1/1992 | Kramer ............................... 215/221 |
| 5,082,130 | 1/1992 | Weinstein ........................... 215/225 |
| 5,115,929 | 5/1992 | Buono ................................ 215/220 |

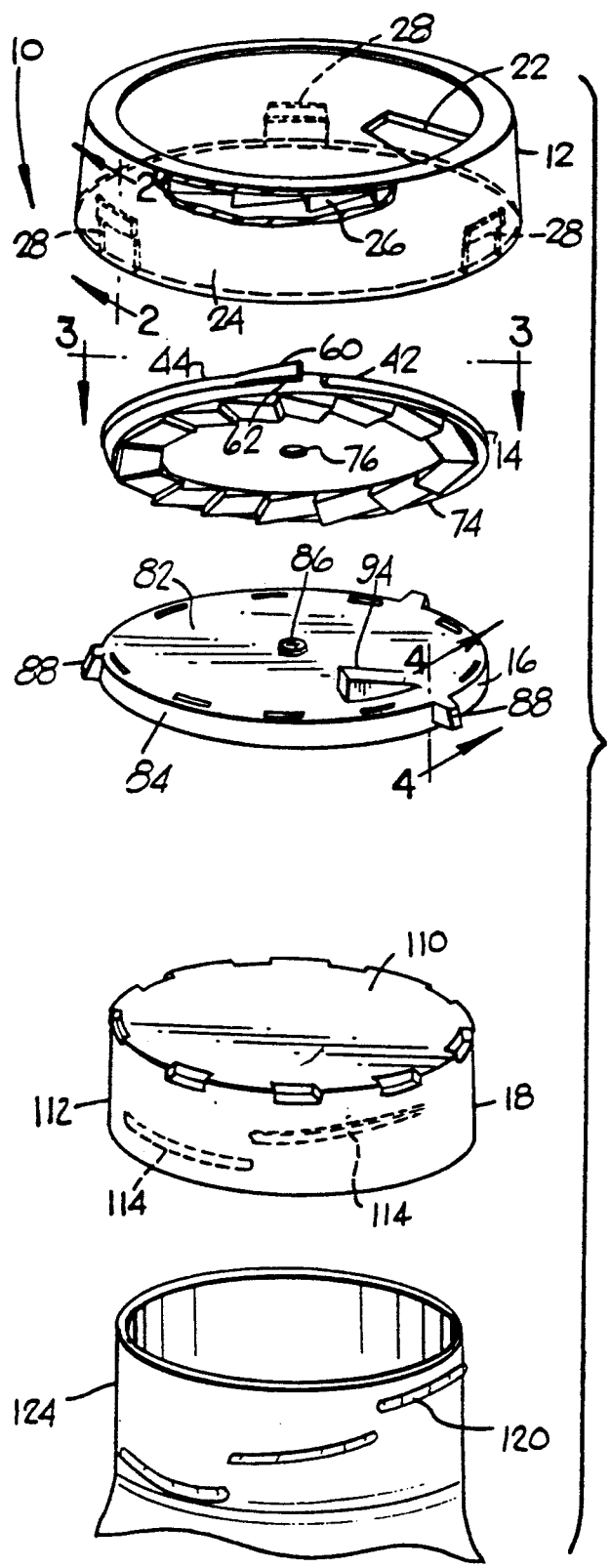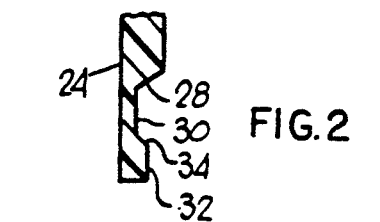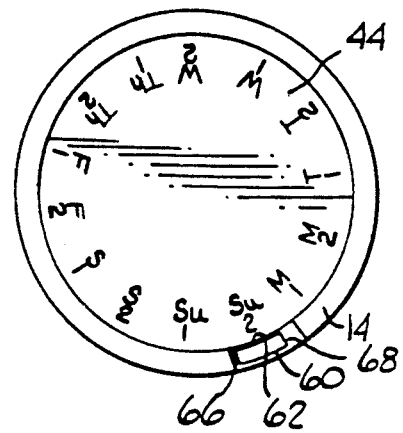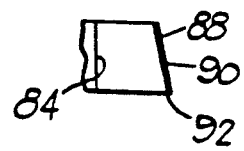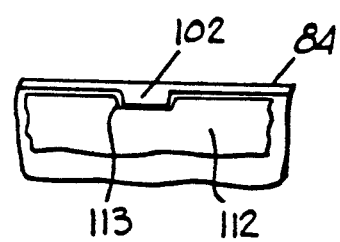

INDICATOR CAP FOR USE WITH THREADED OR BAYONET LUG CONTAINER

This is a continuation of copending application Ser. No. 07/718,354, filed on Jun. 21, 1991, now abandoned, is a continuation-in-part of application No. 07/641,759 filed Jan. 17, 1991, which is a continuation-in-part of application No. 07/306,485 filed Feb. 3, 1989, now U.S. Pat. No. 5,009,338.

BACKGROUND OF THE INVENTION

The present invention relates to closure members for containers, bottles and the like and, more particularly, to closure members having indicator means to indicate the number of times the container has been opened. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, over-utilization may cause side effects or toxicity to a much greater extent than any possible benefit. Thus it is critically important that a patient follow prescribed directions on medications, yet frequently patients forget whether they have taken medication and either omit doses or repeat them.

A considerable number of pill-timing schemes have been used to solve the problem of reminding a patient to take a dose of medicine or reminding him he has already taken the dose. The most used ones involve some scheme of compartmentalization of the necessary medication, such that the pills are placed in compartments that are labeled by day, dose number or time of day, or that are serially numbered. These devices are reasonably satisfactory if a responsible person is available and has the time and patience to fill the compartments properly.

In dispensing pills of a single type, a number of window-containing bottle caps have been invented. Through the window a movable element marked with an index is visible. In only a few devices does the indicating element index in position relative to the window each time the cap is loosened, removed, replaced, and retightened. Thus, by looking at the index mark displayed through the window, a user can see where in repetitive sequence of dose he or she is.

One of the most serious disadvantages of prior art devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users, especially the elderly who may not understand how the device operates, will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. No. 4,011,829 issued Mar. 15, 1977 to Wachsmann, et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of a complicated "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S. Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

The device of European Patent Application No. 87100917.2, published Jul. 27, 1987, by Schwab, has a cup-shaped exterior element that engages a frustoconical closure cap. The Schwab device is somewhat complicated in design and manufacture. The device of U.S. Pat. No. 4,220,247 issued Sep. 2, 1980 to Kramer also includes a cup-shaped exterior element which engages an inner element.

Other devices in the art include U.S. Pat. Nos. 4,511,050 by Nicol; U.S. Pat. No. 4,365,722 by Kramer; U.S. Pat. No. 4,749,093 by Trick; U.S. Pat. No. 4,782,966 by Thackrey; U.S. Pat. No. 4,753,189 by Mastman; U.S. Pat. No. 4,705,182 by Newel-Lewis; U.S. Pat. No. 4,662,520 by Griffen; U.S. Pat. No. 4,641,759 by Kelley; U.S. Pat. No. 4,634,012 by Kelley; U.S. Pat. No. 4,562,933 by Dennis; U.S. Pat. No. 4,528,933 by Allen; U.S. Pat. No. 4,511,050 by Nicol; U.S. Pat. No. 4,548,157 by Hevoyan; U.S. Pat. No. 4,501,370 by Kelley; U.S. Pat. No. 4,489,834 by Thackrey; U.S. Pat. No. 4,432,300 by Lyss; U.S. Pat. No. 4,419,016 by Zoltan; U.S. Pat. No. 4,405,045 by Villa-Real; U.S. Pat. No. 4,357,192 by Moser; U.S. Pat. No. 4,347,804 by Villa-Real; U.S. Pat. No. 4,094,408 by Ford; U.S. Pat. No. 3,996,879 by Walton; U.S. Pat. No. 3,960,713 by Carey; U.S. Pat. No. 3,926,326 by Grau; U.S. Pat. No. 3,921,568 by Fish; U.S. Pat. No. 3,887,099 by Gillman; U.S. Pat. No. 3,753,417 by Garby; U.S. Pat. No. 3,446,179 by Bender; U.S. Pat. No. 3,334,731 by Dale; U.S. Pat. No. 2,943,730 by Tregilgas; U.S. Pat. No. 2,939,597 by Greene; U.S. Pat. No. 2,587,147 by Guion; and U.S. Pat. No. 498,851 by Adsit.

It is thus apparent from a review of this art that there is a need for an improved indicator cap in the manner of the present invention that provides positive controlled movement of the index on both opening and closing of the device, while also providing an indication to the user that the index has functioned properly each time the device is used. Preferably, the basic design of such a device can also be used in other applications where it is necessary to have a record of the number of times a given event occurs.

It is also apparent from a review of this art that there is a need for an improved indicator cap that can be used as a child-resistant closure. Preferably, such a cap would have a minimum of parts, would be easily manufactured and assembled using standard injection molding and assembly methods, and could be used with ordinary containers that are not necessarily specially designed for the cap.

SUMMARY OF THE INVENTION

It is an object of the present invention to provide an indicator device to indicate the number of times a given event has occurred. Such an invention may have applicability in the control of chemical containers, the development of photographic film and many other areas.

More particularly, it is an object of the present invention to provide an indicator cap for a medication dispensing bottle or the like that provides an indication each time the bottle is opened and then reclosed.

It is another object of this invention to provide a device that has positive control of the index member during both the opening and the closing motions and to require the advancement of the index member by one and only one new index during each complete opening and closing cycle.

Yet another object of the invention is to provide an audible sound to confirm that the device has been rotated sufficiently to move the index to the next location and to also provide an audible sound when the device has been rotated sufficiently to re-cock the device for the next open-close sequence.

Still another object is to provide space within the device for the locking mechanisms to slide past each other when not engaged to allow such mechanisms to work reliably over a long period of time.

Another object of the present invention is to combine functions usually requiring several components into single components to reduce the complexity of the device and provide ease of manufacturability and assembly using standard injection molding and assembly techniques.

Another object of the present invention is to provide an indicator assembly that can easily be fitted to an ordinary container without requiring any special modifications to the container itself.

Another object is to provide a device with indicator symbols that can be sensed by touch such as raised letters or braille.

Another object is to provide a device that can be easily grasped by elderly or impaired patients, as by including grasp-facilitating elements on the device.

Another object is to provide a device which is easily manufactured and assembled with a minimum of parts.

A device achieving some of these objects is disclosed in U.S. patent application No. 07/641,759 filed Jan. 17, 1991 (of which the present application is a continuation-in-part) and No. 07/306,485 filed Feb. 3, 1989 (of which the 07/641,759 application is a continuation-in-part), the contents of both of which are hereby incorporated by reference.

BRIEF DESCRIPTION OF THE DRAWINGS

FIG. 1 is an exploded perspective view showing an embodiment of the present invention along with the neck of a container to which the invention can be attached.

FIG. 2 shows a detail of the annular grooves in the outer cover, taken along line 2—2 of FIG. 1.

FIG. 3 shows a detail of the top of the indicator wheel, taken along line 3—3 of FIG. 1.

FIG. 4 shows a detail of the ratchet wheel tabs, taken along line 4—4 of FIG. 1.

FIG. 5 shows a detail of the lugs and notches of the ratchet wheel and sealing cover of FIG. 1.

DESCRIPTION OF THE PREFERRED EMBODIMENTS

Four-Piece Threaded Version. A preferred embodiment of the invention 10 is shown in FIG. 1. This preferred embodiment includes an outer cover 12, an indicator wheel 14, a ratchet wheel 16 and an inner cover 18. The outer cover includes a top circular portion with a window 22 and a depending skirt 24. The lower surface of the top circular portion 20 has a set of teeth 26.

The inner surface of the depending skirt 24 has a set of grooves 28 (three in the embodiment shown), as better seen in FIG. 2. The grooves 28 are in the annular direction around a portion of the depending skirt inner surface, and include a deep groove portion 30 and a shallow groove portion 32 connected by a ramp 34 which may be perpendicular to the two groove portions or may be sloped relative to the two groove portions. The function of the grooves is to receive the ratchet wheel tabs as described in some detail below.

The window 22 in the circular top portion 20 of the outer cover 12 may be trapezoidal in shape as shown in FIG. 1 or, alternatively, may be circular in shape or may be circular on its upper edge and sloped to trapezoidal on its lower edge. In the later alternative especially, the window can be used with an indicator wheel having raised or recessed alpha-numeric symbols or braille symbols so that the user can sense the symbols with his finger even though his vision may be physiologically or environmentally impaired.

The indicator wheel 14 includes a circular top portion 42 containing a set of indicator symbols 44 to indicate a day of the week and a dose number of that day. For example, the symbols may be Su1, Su2, M1, M2, etc. as shown in FIG. 3 to indicate a dosage schedule of two per day. Alternatively, of course, the indicator symbols may be 1, 2, 3, 1, 2, 3, etc. to indicate a dosage schedule of three per day, or Su, M, Tu, etc. to indicate a dosage schedule of one per day, and so on.

The total number of indicator symbols 44 on the indicator wheel 14 should be evenly divisible into the total number of teeth 26 in the outer cover 12. Otherwise, the indicator symbols will not advance one at a time past the outer cover window 22 as the device is operated unless the indicator wheel has some blanks in place of indicator symbols. Preferably, the number of indicator symbols 44 together with the number of any blanks that may be necessary is exactly equal to the number of outer cover teeth 26.

In the region of the outer perimeter of the indicator wheel 14 is a ratchet 60 which is spaced apart from the body of the indicator wheel by a space 62 underneath it, an annular slot on the radially inner side of it, and a leading edge slot 66 adjacent the leading edge of it. The ratchet is flexibly connected to the indicator wheel of only the trailing edge 68. This flexible connection along with the annular slot and the slot 66 and space 62 allow the ratchet to flex as it passes over the outer cover teeth 26 of the outer cover 12.

The bottom surface of the indicator wheel 14 includes a set of indicator wheel teeth 74. The number of indicator wheel teeth involves the same considerations as the number of outer cover teeth, as discussed above, and preferably is exactly equal to the total of the number of indicator symbols and the number of blanks on the upper circular portion of the indicator wheel. The bottom surface of the indicator wheel 14 also preferably has an axially extending center hole 76 to receive the hub of the ratchet wheel in the manner described below.

The ratchet wheel 16 includes a circular upper portion 82 and a depending skirt 84. The center of the circular upper portion 82 has an axially extending center hub 86 which mates with the center hole 76 of the indicator wheel. Around the outer circumference of the circular upper portion 82 is a set of tabs 88 extending radially outward. As better seen in FIG. 4, the tabs 88 have a sloping ramp 90 and a locking edge 92 at the lower end of the sloping ramp 90. The tabs 88 engage the grooves 28 in the inner surface of the depending skirt 24 of the outer cover 12 and, therefore, are numbered and configured to align therewith so that the ratchet wheel can be attached to the outer cover by the tabs and grooves while still allowing a predetermined amount of rotation of one relative to the other by sliding the tabs annularly through the grooves.

The ratchet wheel also includes a ratchet wheel pawl 94 flexibly attached to the circular upper portion 82. The pawl 94 rests in and is attached to one end of a rectangular cutout in the circular upper portion to allow it to flex up and down as it rides over the indicator wheel teeth 74 on the bottom of the indicator wheel 14.

Another element of the ratchet wheel 16 is a set of lugs 102 extending downward from the lower surface and radially inward from the depending skirt 84. The lugs 102 occupy a space at the joining of the circular upper portion 82 (on its lower side) and the depending skirt 84 (on its inner side) and are numbered and configured to mate with the notches on the upper surface of the sealing cover as described below.

The sealing cover 18 includes a circular upper portion 110 and a depending skirt 112. The circular upper portion 110 has a set of notches 113 numbered and configured to mate with the lugs 102 on the ratchet wheel 16 and are better shown in FIG. 5. The purpose of the lugs and notches are to engage the ratchet wheel with the sealing cover upon the application of an axial force pushing the two together when the device is turned in the direction to unscrew it from the container. The lugs and notches are configured such that no axial force (other than that provided by gravity) is required to engage them when the device is turned in the direction to screw it onto the container. It can be appreciated that the exact number and configuration of the lugs and notches is not critical so long as they effectively engage one another upon the application of an axial force within the easy capability of an adult, and they disengage upon the release of such force. Lug and notch arrangements such as this are well-known in the field of child-resistant closures, and need not be described in any more detail here. The inner surface of the depending skirt 112 of the sealing cover 18 has threads 114 to mate with threads 120 on the outer surface of the neck of the container 124.

Although the embodiment shown has teeth on the lower surface of the indicator wheel and a mating pawl on the upper surface of the ratchet wheel, the arrangement could also be reversed so that the pawl is on the lower surface of the indicator wheel and the teeth are on the upper surface of the ratchet wheel. Similarly, the teeth on the outer cover and the pawl on the indicator wheel could be reversed so that the pawl is on the outer cover and the teeth are on the indicator wheel, and the grooves on the outer cover and tabs on the ratchet wheel could be reversed so that the grooves are on the ratchet wheel and the tabs are on the outer cover. Finally, the direction of the teeth and pawls may be reversed, so that the indicator wheel advances when the device is closed rather than when it is opened. The possibility of reversing the elements in these ways applies to all of the embodiments described herein. Whether the elements should be reversed or not may depend on molding and assembly considerations. Also, the mating pawls may include a plurality of pawls or even an entire set of pawls such as a circumferential row of teeth. Alternatively, the teeth with which the pawls mate may be replaced by holes or other depressions or other means for engagement.

In operation, the preferred embodiment 10 of FIGS. 1–5 can be attached to the container 124 by placing it onto the top of the container and turning it in a clockwise direction (or counterclockwise direction if the threads were left-handed). The turning of the outer cover 12 is translated into a turning of the indicator wheel 14 by the outer cove teeth 26 engaging the indicator wheel pawl 60.

The turning of the indicator wheel 14 is translated into a turning of the ratchet wheel 16 by the outer cover grooves 28 engaging the ratchet wheel tabs 88. First, however, the outer cover 12 must be turned sufficiently so that the wall of the outer cover grooves 28 contacts the ratchet wheel tabs 88. Until the outer cover is turned that necessary amount, the tabs slide through the grooves, and the rotating indicator wheel slides over the stationary ratchet wheel. The sliding of the indicator wheel over the ratchet wheel causes the ratchet wheel pawl 94 to slide over the indicator wheel teeth 74, causing an audible click when the pawl snaps over a tooth to confirm the proper operation of the device.

Once the outer cover is turned sufficiently so that the ratchet wheel tabs are against the end wall of the outer cover grooves, the ratchet wheel begins to turn. The turning of the ratchet wheel is translated into a turning of the sealing cover 18 by the ratchet wheel lugs 102 engaging the sealing cover notches 113. As the sealing cover 18 turns relative to the container 124, the sealing cover threads engage the container threads to close and seal the container.

To remove the device 10 from the container, it is turned in the opposite direction relative to the container while an axial force is applied urging the outer cover 12 toward the container 124 in order to engage the ratchet wheel lugs 102 with the sealing cover notches 113. The initial turning of the outer cover 12 will not be translated into a turning of the sealing cover 18, however. Instead, the indicator wheel 14 will remain stationary as an outer cover tooth 26 slides over the indicator wheel pawl 60. This sliding will advance the outer cover window 22 to a new indicator symbol, thereby recording that the device has been opened. As the window advances one full indicator symbol, the indicator wheel pawl 60 will pass over one complete outer cover tooth 26 and, when it does, the pawl will snap over the edge of the tooth. This results in an audible click confirming the proper window advancement.

Also stationary during the initial turning of the outer cover 12 is the ratchet wheel 16. This is because the ratchet wheel tabs 88 slide through the outer cover grooves 28. At the same time, the ratchet wheel pawl 94 engages the indicator wheel teeth 74 to prevent any movement between the indicator wheel and ratchet wheel.

When the ratchet wheel tabs 88 finally have slid through the outer cover grooves 28 so that the tabs are against an end wall of the grooves, the groove end wall applies a force against the tabs so that the ratchet wheel 16 begins to turn with the outer cover 12. This turning of the ratchet wheel 16 translates into a turning of the sealing cover 18, provided that the necessary axial force is applied to maintain the engagement between the ratchet wheel lugs 102 and sealing cover notches 113. The sealing cover threads 114 then unscrew from the container threads 120 to allow the device 10 to be removed from the container. The device is at that time in a proper configuration to be put back onto the container, with the indicator wheel tabs 88 at one end of the outer cover grooves 28.

What is claimed is:

1. A child resistant indicator closure for placing over and closing a container, comprising:
   (a) indicating means including an outer cover having a top portion with a window and a circumferential depending skirt extending downward from the top portion, an indicator symbol carrier positioned below the top portion of the outer cover and having indicator symbols selectively visible through said window, outer cover engagement means for rotatably engaging the outer cover with the indicator symbol carrier, a retainer positioned below the indicator symbol carrier, retainer engagement means for rotatably engaging the retainer with the indicator symbol carrier, and limited motion means for allowing limited rotation between the retainer and the outer cover;
   (b) closing means rotatably attached to said indicating means for attaching the closure to a container including a cap threadably attachable to the container and positioned below the retainer; and
   (c) child-resistant means for resisting the removal of the closure from the container by a child including a set of lugs on one of the cap and the retainer and a set of mating notches on the other of the cap and the retainer, whereby a force urging the closure toward the container is necessary to engage the lugs with the mating notches to effect a rotation of the cap upon a rotation of the indicating means.

2. The closure of claim 1 wherein:
   (a) the outer cover engagement means includes a set of outer cover engagement means teeth on one of the outer cover and indicator symbol carrier, and an outer cover engagement means pawl mounted on the other of the outer cover and the indicator symbol carrier, the outer cover engagement means pawl being engaged with the set of outer cover engagement means teeth to allow rotation of the outer cover relative to the indicator symbol carrier in a first direction but not in a second direction opposite the first direction; and
   (b) the retainer engagement means includes a set of retainer engagement means teeth on one of the indicator symbol carrier and the retainer, and a retainer engagement means pawl mounted on the other of the indicator symbol carrier and retainer, the retainer engagement means pawl being engaged with the set of retainer engagement means teeth to allow rotation of the indicator symbol carrier relative to the retainer in said second direction but not in said first direction.

3. The closure of claim 2, wherein at least one of said pawls is flexibly mounted.

4. The closure of claim 3, wherein at least one of said pawls abruptly unflexes to produce an audible click confirming the advancement of the pawl.

5. The closure of claim 2, wherein said pawls do not flex.

6. A child-resistant indicator closure for placing over and closing a threaded container comprising:
   (a) an indicator including an outer cover having a top portion with a window and a circumferential depending skirt extending downwardly from the top portion, an indicator symbol carrier positioned below the top portion of the outer cover and having indicator symbols selectively visible through said window, a first, rotatable engagement between the outer cover and the indicator symbol carrier, a retainer positioned below the indicator symbol carrier, a second, rotatable, engagement between the retainer and the indicator symbol carrier, and a third rotatable engagement between the retainer and the outer cover, the third engagement permitting only limited rotation between the outer cover and the retainer;
   (b) a cap rotatably attached to the indicator, the cap being positioned below the retainer and being threaded to matingly attach with the container; and
   (c) a set of lugs on one of the cap and the retainer and a set of mating notches on the other of the cap and the retainer, the lugs and notches being positioned with respect to one another such that a force is required urging the closure towards the container to engage the lugs with the mating notches to effect a rotation of the cap upon a rotation of the indicator.

7. A closure of said claim 6 wherein:
   (a) the first engagement includes a set of first engagement teeth on one of the outer cover and the indicator symbol carrier, and a first engagement pawl mounted on the other of the outer cover and the indicator symbol carrier, the first engagement pawl being positioned to engage with the set of first engagement teeth to allow rotation of the outer cover relative to the indicator symbol carrier in a first direction but not in a second direction opposite the first direction; and
   (b) the second engagement including a second set of engagement teeth on one of the indicator symbol carrier and the retainer and a second engagement pawl mounted on the other of the indicator symbol carrier and retainer, the second engagement pawl being positioned to engage with the second set of engagement teeth to allow rotation of the indicator symbol carrier relative to the retainer in the second direction but not in the first direction.

* * * * *